US009924865B2

(12) United States Patent
Alnajar et al.

(10) Patent No.: US 9,924,865 B2
(45) Date of Patent: Mar. 27, 2018

(54) APPARATUS AND METHOD FOR ESTIMATING GAZE FROM UN-CALIBRATED EYE MEASUREMENT POINTS (71) Applicants: UNIVERSITEIT VAN AMSTERDAM, Amsterdam (NL); SIGHTCORP B.V., Amsterdam (NL)

(72) Inventors: Fares Alnajar, Amsterdam (NL); Roberto Valenti, Amsterdam (NL); Theo Gevers, Amsterdam (NL)

(73) Assignees: UNIVERSITEIT VAN AMSTERDAM, Amsterdam (NL); SIGHTCORP B.V., Amsterdam (NL)

( * ) Notice: Subject to any disclaimer, the term of this patent is extended or adjusted under 35 U.S.C. 154(b) by 17 days.

(21) Appl. No.: 15/100,228

(22) PCT Filed: Nov. 28, 2014

(86) PCT No.: PCT/EP2014/076026
§ 371 (c)(1),
(2) Date: May 27, 2016

(87) PCT Pub. No.: WO2015/079054
PCT Pub. Date: Jun. 4, 2015

(65) Prior Publication Data
US 2017/0007118 A1    Jan. 12, 2017

(30) Foreign Application Priority Data
Nov. 29, 2013 (EP) .................................... 13195179

(51) Int. Cl.
G06K 9/00 (2006.01)
A61B 3/113 (2006.01)
(Continued)

(52) U.S. Cl.
CPC .............. *A61B 3/113* (2013.01); *G06F 3/013* (2013.01); *G06F 17/18* (2013.01)

(58) Field of Classification Search
CPC .......... A61B 3/113; G06F 17/18; G06F 3/013
See application file for complete search history.

(56) References Cited

U.S. PATENT DOCUMENTS 5,604,818 A  *  2/1997  Saitou ....................... G06T 7/70
                                                          348/78
6,359,601 B1 *  3/2002  Maguire, Jr. ........... G06F 3/013
                                                          345/7
(Continued)

FOREIGN PATENT DOCUMENTS

WO    2012055444 A1    5/2012
WO    2013059940 A1    5/2013
WO    2013149966 A1    10/2013

OTHER PUBLICATIONS

International Search Report and Written Opinion issued in International Application No. PCT/EP2014/076026.
(Continued)

Primary Examiner — John Strege
(74) Attorney, Agent, or Firm — Kenealy Vaidya LLP (57) ABSTRACT Some embodiments are directed to a system and a method for estimating gaze from a set of eye measurement points that are indicative of a gaze pattern of a user viewing a scene. Some other embodiments are directed to obtaining sets of eye measurement points from different users viewing the same scene. In another embodiment, the different sets of eye measurement points are mapped to a common coordinate system for reciprocal calibration In yet another embodiment, a scene transformation for mapping the common coordinate system to a coordinate system associated with the scene can be calculated by matching eye measurement points from the common coordinate system to interest points (Continued)

of the scene. The scene transformation is thereby calculated more accurately than individually calculated scene transformations, thereby providing a more accurate estimate of the gaze points.

15 Claims, 4 Drawing Sheets

(51) Int. Cl.
*G06F 3/01* (2006.01)
*G06F 17/18* (2006.01)

(56) References Cited

U.S. PATENT DOCUMENTS

| | | | |
|---|---|---|---|
| 6,381,339 B1 * | 4/2002 | Brown | G06F 3/013 382/100 |
| 6,758,563 B2 * | 7/2004 | Levola | A61B 3/113 351/209 |
| 7,657,062 B2 * | 2/2010 | Pilu | A61B 3/113 345/8 |
| 2010/0295774 A1 | 11/2010 | Hennessey | |
| 2015/0092983 A1 * | 4/2015 | Nguyen | G06F 3/013 382/103 |
| 2016/0029883 A1 * | 2/2016 | Cox | G06F 3/013 351/209 |
| 2016/0092743 A1 * | 3/2016 | Lee | G02B 27/0093 348/78 |
| 2016/0156850 A1 * | 6/2016 | Werblin | G06F 3/013 348/63 |

OTHER PUBLICATIONS

Tilke Judd, et al., 'Learning to Predict Where Humans Look', Computer Vision, 2009 IEEE 12th International Conference on, IEEE, Piscataway, NJ, USA, Sep. 29, 2009 (Sep. 29, 2009), pp. 2106-2113.

* cited by examiner

APPARATUS AND METHOD FOR ESTIMATING GAZE FROM UN-CALIBRATED EYE MEASUREMENT POINTS

CROSS REFERENCE TO RELATED APPLICATION

This application is a U.S. National Phase filing under 35 C.F.R. § 371 of, and claims priority to, International PCT patent application No.: PCT/EP2014/076026, filed on Nov. 28, 2014, which claims priority to European Patent Application No.: 13195179.0, filed on Nov. 29, 2013, the contents of each of which are hereby incorporated in their entireties by reference.

FIELD OF THE INVENTION

The invention relates to a system and a method for enabling estimating gaze from a set of un-calibrated eye measurement points.

The invention further relates to a computer program product comprising instructions for causing a processing subsystem to perform the method.

BACKGROUND ART

Gaze estimation refers to the process of determining where a person is looking at in a predefined plane, i.e., a gaze plane. Such a gaze plane may be associated with a scene, such as, e.g., a physical scene as presented in a shopping window, or a virtual scene as provided by content displayed on a computer screen. Here, the points at which a person gazes at in the scene are referred to as gaze points. Gaze estimation is increasingly important for many applications such as human-computer interaction, marketing and advertisement, and human behavior analysis.

Gaze estimation methods generally involve calibration. The calibration may be camera-based (estimating the camera parameters), geometric calibration (estimating the relations between the scene components like the camera, the gaze plane, and the user), or personal calibration (determining the angle between visual and optical axes). An extensive overview of the different approaches of gaze estimation and their calibration can be found in "*In the Eye of the Beholder: A Survey of Models for Eyes and Gaze*" by D. W Hansen et al., IEEE Transactions on Pattern Analysis and Machine Intelligence, Vol. 32, Issue 3, p. 478-500, 2010.

During calibration, users are usually asked to fixate their gaze on certain points in a scene while images of their eyes are captured. This procedure is cumbersome and sometimes impractical. For example, when tracking costumer's attention in shops, estimating the gaze points or regions should be done passively, i.e., without the user having to actively take part in a calibration.

It is known to use statistical data of eye movement measurements to enable such passive gaze estimation. For example, U.S. Pat. No. 7,657,062 B2 provides a calibration apparatus for automatically self-calibrating a set of eye tracking measurements to a reference space, said apparatus comprising: a tracking device capable of capturing a plurality of eye gaze measurements, representing a plurality of eye gaze positions; a statistical analyzer for determining a statistical distribution of said plurality of eye gaze measurements; a data storage device for storing a predetermined set of statistics data of eye movement measurements; a statistical data comparison component for comparing said statistical distribution data of said plurality of eye gaze measurements with said stored predetermined set of statistical data of eye movement measurements; and a calibration data generating component for generating a calibration data depending upon a result of said comparison.

Hence, U.S. Pat. No. 7,657,062 B2 uses statistical distribution data of which the relation to the reference space is known to calibrate the eye gaze measurements of a user. It is mentioned that the predetermined statistics may take two forms. Firstly, a set of statistics may be taken for a plurality of persons in order to obtain an "average" statistical information for human users, describing the eye movement patterns of a notional average person. Such statistics are not specific to any one individual person, but may represent a notional average person based upon an average of a test sample comprising a plurality of persons. FIG. 6 of U.S. Pat. No. 7,657,062 B2 shows that the notional average person gazes straight ahead with the highest probability. Secondly, statistics may be derived for measurements taken from just one individual person. In this case, the individual person may have their own particular quirks and idiosyncrasies.

WO 2013/059940 A1 describes a method for automating a gaze tracking system calibration based on display content and/or user actions that are likely to attract the subject's gaze. The method involves obtaining gaze data, obtaining at least one key point corresponding to a portion of media content being displayed, linking the gaze data to the at least one key point, and generating one or more calibration parameters by comparing gaze data with associated ones of the at least one key point Disadvantageously, U.S. Pat. No. 7,657,062 B2 and WO 2013/059940 A1 each provide a relatively inaccurate estimation of the gaze of a user viewing a scene.

SUMMARY OF THE INVENTION

One of the objects of the invention is to obtain a system or method which enables the gaze of a user viewing a scene to be more accurately estimated.

The following aspects of the invention are based on the insight that gaze patterns between different users are similar for a same scene. Here, the term 'gaze pattern' refers to the spatial distribution of gaze points with respect to the scene. As such, the eye measurement points of a user viewing a scene can be calibrated to the eye measurement points of another user viewing, or having viewed, the same scene. Hence, users do not need to actively participate in the calibration procedure.

A first aspect of the invention provides a system for enabling estimating gaze of different users with respect to a scene from eye measurement points which represent un-calibrated eye measurements of the users viewing the scene, the system comprising:

an input for obtaining at least a first set of eye measurement points of a first user viewing the scene and a second set of eye measurement points of a second user viewing the scene, the first set of eye measurement points being obtained as coordinates in a first coordinate system, the second set of eye measurement points being obtained as coordinates in a second coordinate system, the first coordinate system and the second coordinate system having an unknown geometric relation;

a processing subsystem configured for:
  i) mutually calibrating the first set of eye measurement points and the second set of eye measurement points by mapping said points to a common coordinate system, thereby obtaining a set of mapped eye measurement points, said mapping comprising establishing a coordinate transformation which provides similar coordinates in the common coordinate system for geometrically similar topologies of both sets of eye measurement points; and ii) calculating a scene transformation for mapping the common coordinate system to a coordinate system associated with the scene, said calculating comprising matching eye measurement points from the set of mapped eye measurement points to interest points of the scene.

A further aspect of the invention provides a method for enabling estimating gaze of different users with respect to a scene from eye measurement points which represent un-calibrated eye measurements of the users viewing the scene, the method comprising:

obtaining at least a first set of eye measurement points of a first user viewing the scene and a second set of eye measurement points of a second user viewing the scene, the first set of eye measurement points being obtained as coordinates in a first coordinate system, the second set of eye measurement points being obtained as coordinates in a second coordinate system, the first coordinate system and the second coordinate system having an unknown geometric relation;

mutually calibrating the first set of eye measurement points and the second set of eye measurement points by mapping said points to a common coordinate system, thereby obtaining a set of mapped eye measurement points, said mapping comprising establishing a coordinate transformation which provides similar coordinates in the common coordinate system for geometrically similar topologies of both sets of eye measurement points; and calculating a scene transformation for mapping the common coordinate system to a coordinate system associated with the scene, said calculating comprising matching eye measurement points from the set of mapped eye measurement points to interest points of the scene.

A further aspect of the invention provides a computer program product comprising instructions for causing a processor system to perform the method.

The above measures involve obtaining at least two sets of eye measurement points of different users viewing the same scene. Each set of eye measurement points is indicative of the gaze pattern of a respective user when the user is viewing the scene in that they represent un-calibrated measurements from which a set of gaze points may be calculated, i.e., by calibration. For example, the eye measurement points may represent changes in the user's eyes when viewing the scene. Such changes may be measured using, e.g., a video camera, a depth camera, infrared diodes, etc. As such, the eye measurement points may represent gaze directions, relative iris movements or changes in descriptors extracted from the eyes. However, the eye measurement points may also take any other suitable form.

Both sets of eye measurement points are defined as coordinates in coordinate systems which have an unknown geometric relation. For example, the eye measurement points may be provided as Cartesian coordinates in planes having differently defined axes. As the geometric relation between the coordinate systems is not (entirely) known, both sets of eye measurement points are mutually un-calibrated in that the same coordinates in both coordinate systems may represent different measured quantities of both users, e.g., different gaze directions or different relative iris movements, and thus represent different gaze points with respect to the scene.

A processing subsystem is provided for mapping the first set of eye measurement points and the second set of eye measurement points to a common coordinate system. In obtaining such a mapping, the processing subsystem ensures that similar coordinates in the common coordinate system are established for the geometrically similar topologies of both sets of eye measurement points. Here, the term 'topology', and in particular 'geometric topology', refers to the geometric relation between the eye measurement points, as indicated by, e.g., their relative position, their relative distance, etc. In other words, the geometric topology represents the spatial inter-relations and arrangement of eye measurement points.

Moreover, the processing subsystem calculates a scene transformation for mapping the common coordinate system to a coordinate system associated with the scene. This calculation is performed on the basis of the processing subsystem matching eye measurement points from the common coordinate system to interest points of the scene. Here, the term 'interest point' refers to a point in the scene which is expected to draw a user's attention. For example, a linear transformation may be calculated which minimizes a distance measure being defined as a function of the distance between the eye measurement points and the interest points of the scene.

The inventors have recognized that different users exhibit similar gaze patterns when viewing a same scene. This assumption is supported by the publication "*Learning to predict where humans look*" by Judd, K. Ehinger et al, IEEE International Conference on Computer Vision (ICCV), p. 2106-2113, 2009, in which the authors describe a database of (calibrated) eye tracking data which shows that the gaze patterns of previous users are predictive of those of new users viewing same scene. The invention makes use of the above recognition in that geometrically similar topologies in the eye measurement points of different users are assumed to represent a similar gaze pattern with respect to the scene. Accordingly, eye measurement points of different users may be mutually calibrated by mapping the eye measurement points to a common coordinate system in which the geometrically similar topologies match in coordinates, i.e., at least partially overlap. As a result, similar measured quantities of the different users, e.g., similar gaze directions or similar relative iris movements, are mapped to similar coordinates in the common coordinate system. Accordingly, after mapping, the eye measurement points of the different users are mutually calibrated.

The above measures have the effect that a calibration between the eye measurement points of a particular user and the scene is obtained by mapping the user's eye measurement points together with those of at least one other user jointly to a common coordinate system. The scene transformation is then calculated based on eye measurement points which have been mapped to the common coordinate system.

The inventors have recognized that this allows the eye measurement points of a single user to be more accurately calibrated since after said mapping, distinct patterns emerge in the common coordinate system which allow the mapping to the interest points to be more accurately calculated. Advantageously, the mapping of the eye measurement points of different users to a single coordinate system reduces the influence of individual outliers in the eye measurement points of each user. In contrast, when mapping the eye measurement points of each user individually to such interest points, it is not or less apparent which eye measurement points constitute outliers in the measurement, resulting in such individually calculated transformations to be less accurate. In this respect, it is noted that U.S. Pat. No. 7,657,062 B2 does not mutually calibrate eye measurement points relating to the viewing of a same scene but rather makes use of non-scene specific statistical data. Disadvantageously, U.S. Pat. No. 7,657,062 B2 obtains a less accurate calibration.

It is noted that the above measures enable estimating gaze from a set of eye measurement points of the first user or the second user, in that a set of gaze points can be obtained when applying the scene transformation to the set of eye measurement points after being mapped to the common coordinate system.

Optionally, the input is arranged for obtaining a further set of eye measurement points of a further user viewing the scene, the further set of eye measurement points being obtained as coordinates in a coordinate system having an unknown geometric relation with the common coordinate system, and the processing subsystem is configured for estimating a set of gaze points from the further set of eye measurement points by:
  i) mapping the further set of eye measurement points to the common coordinate system based on said establishing of similar coordinates for geometrically similar topologies, thereby obtaining a further set of mapped eye measurement points; and
  ii) estimating the set of gaze points of the further user by applying the scene transformation to the further set of mapped eye measurement points Accordingly, the eye measurement points of each further user viewing the scene may be automatically mutually calibrated with respect to those of other users viewing the scene by mapping the eye measurement points to the common coordinate system. Here, the mapping makes use of the abovementioned recognition that geometrically similar topologies in the eye measurement points of different users are assumed to represent a similar gaze pattern with respect to the scene. The same scene transformation may then be used to estimate the set of gaze points from the further set of mapped eye measurement points. It is therefore not needed to calculate the scene transformation anew for each further individual user viewing the scene.

It is noted that a same effect may be obtained by, instead of performing the above steps i) and ii), performing the following steps j) and jj):
  j) applying the scene transformation to mapped eye measurement points of the common coordinate system to obtain a reference set of gaze points; and
  jj) estimating the set of gaze points of the further user by mapping the further set of eye measurement points directly to the coordinate system of the scene based on said establishing of similar coordinates for geometrically similar topologies between the reference set of gaze points and the set of gaze points of the further user.

Optionally, the processing subsystem is configured for combining the set of mapped eye measurement points and the further set of mapped eye measurement points to obtain a set of reference points, and wherein said mapping of the further set of eye measurement points to the common coordinate system is performed by the processing subsystem matching geometrically similar topologies between the further set of eye measurement points and the set of reference points.

By combining the set of mapped eye measurement points and the further set of mapped eye measurement points in the common coordinate system, a set of reference points is obtained. Such combining enables the influence of individual outliers to be explicitly reduced, e.g., by omitting or flagging such outliers. Effectively, the set of reference points may represent an estimate of the common interest points of different users, which may then be mapped to the (actual) interest points in the scene. Advantageously, the set of gaze points may be more accurately estimated.

Optionally, the processing subsystem is configured for combining the set of mapped eye measurement points and the further set of mapped eye measurement points by applying a statistical filter to both sets of eye measurement points. Statistical filters, such as rank-order filters, enable the individual outliers in the eye measurement points of different users to be effectively reduced.

Optionally, the processing subsystem is configured for including the further set of mapped eye measurement points in the set of reference points so as to iteratively buildup the set of reference points. By including further sets of eye measurement points in the set of reference points, the influence of individual outliers may be further reduced.

Optionally, the processing subsystem is configured for re-calculating the scene transformation after said including of the further set of mapped eye measurement points. By updating the scene transformation, the accuracy of the scene transformation may be improved since the influence of individual outliers may have been further reduced by the inclusion of the further set of mapped eye measurement points. Advantageously, the system may use the eye measurement points of new users viewing the scene to gradually provide a more accurate estimation of their gaze.

Optionally, the processing subsystem is configured for identifying a difference between the set of gaze points of the further user and a reference set of gaze points which is obtained by applying the scene transformation to the set of reference points. Differences between the gaze points of users may be highly relevant. For example, when viewing a shopping window, such differences may reflect individual preferences of users. By identifying such differences in the gaze points, the individual preferences are made visible. These may be used to later on dynamically customize the scene to each user.

Optionally, the difference comprises at least one of: a difference in temporal order of gazing at same or similar parts of the scene, and a difference in the parts of the scene at which the gazing is directed. The order in which a user gazes at same or similar parts of the scene may reflect their individual preferences, as does the difference in the parts of the scene at which the user's gazing is directed.

Optionally, the first set of eye measurement points and the second set of eye measurement points are obtained from users viewing different instances of the scene. The system thus combines the measurement data of users viewing different instances of the scene rather than viewing the same instance of the scene at different times. Advantageously, if there exist such different instances of a scene, the measurement data obtained at said scenes may be combined since the users are nevertheless expected to exhibit similar gaze patterns with respect to the scenes.

Optionally, the different instances of the scene comprise at least one of: the scene at different locations, a display of the scene provided by different display devices, different types of physical display of the scene. Advantageously, the measurement data across different locations, different display devices or different types of physical display of the scene may be combined. Here, the term 'different types of physical display' refers to the scenes being displayed using different physical principles, e.g., using printed paper vs. using a digital screen.

Optionally, the system further comprises a first eye measurement subsystem for obtaining the first set of eye measurement points of the first user viewing a first instance of the scene, and a second eye measurement subsystem for obtaining the second set of eye measurement points of the second user viewing a second instance of the scene, the first instance being different from the second instance. As a consequence of relating to different instances of the scene, the eye measurement subsystems are located at different locations, and/or are differently arranged so as to obtain the measurements with respect to the scene provided by different display devices, and/or provided by different types of physical display of the scene.

Optionally, the input is arranged for obtaining an image of the scene, and the processing subsystem is configured for using a saliency detection technique to detect saliency points in the image so as to determine the interest points of the scene. By obtaining an image of the scene and detecting saliency points in the scene, it is not needed to manually annotate or otherwise determine the interest points of the scene.

Optionally, the mapping of the first set of eye measurement points and the second set of eye measurement points to the common coordinate system comprises a linear coordinate transformation. A linear coordinate transformation is well suited for mapping the eye measurement points to a common coordinate system in which the geometrically similar topologies match in coordinates, i.e., at least partially overlap, while still allowing for individual differences in the eye measurement points. For example, the transformation may comprise translation, rotation, shearing and scaling.

Optionally, each set of eye measurement points is constituted by a measurement of one of the group of: a gaze direction, an iris movement and a position of part of the eyes. The system may use various types of measurement data, including but not limited to measurement data of the aforementioned types.

In summary, the invention enables estimating gaze from a set of eye measurement points which are indicative of a gaze pattern of a user viewing a scene. Herein, use is made of the insight that gaze patterns of different users are similar for a same scene. The invention involves obtaining different sets of eye measurement points from different users viewing the same scene. The different sets of eye measurement points are mapped to a common coordinate system, and thereby mutually calibrated, based on the assumption that geometrically similar topologies between the different sets of eye measurement points are to be mapped to similar coordinates in the common coordinate system as they represent a similar or same gaze pattern. A scene transformation for mapping the common coordinate system to a coordinate system associated with the scene can be calculated by matching eye measurement points from the common coordinate system to interest points of the scene. The scene transformation is thereby calculated more accurately than individually calculated scene transformations, thereby providing a more accurate estimate of the gaze points.

It will be appreciated by those skilled in the art that two or more of the above-mentioned embodiments, implementations, and/or optional aspects of the invention may be combined in any way deemed useful.

The invention is defined in the independent claims. Advantageous embodiments are defined in the dependent claims.

BRIEF DESCRIPTION OF THE DRAWINGS

These and other aspects of the invention are apparent from and will be elucidated with reference to the embodiments described hereinafter. In the drawings.

It should be noted that items which have the same reference numbers in different Figures, have the same structural features and the same functions, or are the same signals. Where the function and/or structure of such an item has been explained, there is no necessity for repeated explanation thereof in the detailed description.

DETAILED DESCRIPTION OF EMBODIMENTS

Figure 1:
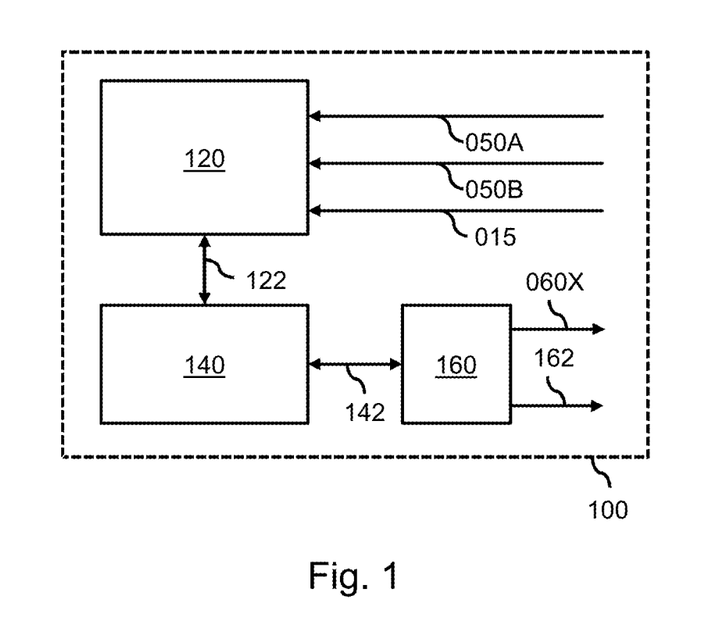
FIG. 1 shows a system in accordance with the present invention, the system being arranged for enabling estimating gaze from at least two set of eye measurement points of respective users viewing a same scene.

FIG. 1 shows a system 100 comprising an input 120 for obtaining at least a first set of eye measurement points 050A of a first user viewing a scene and a second set of eye measurement points 050B of a second user viewing the scene. Here, each set of eye measurement points is indicative of a gaze pattern of the respective user when viewing the scene. Such sets of eye measurement points may be obtained in various ways. For example, the system 100 may be connected to a measurement system (not shown in FIG. 1) which measures, in real-time when a user views the scene, a change in the user's relative iris movement, a change in the position of the user's eyes, etc. Alternatively or additionally, such measurement data 050A, 050B may be obtained from a database and represent a previously measured set of eye measurement points. The input 120 may constitute or be part of, e.g., a network interface or a storage interface.

The first set of eye measurement points 050A are obtained as coordinates in a first coordinate system and the second set of eye measurement points 050B are obtained as coordinates in a second coordinate system. The first coordinate system and the second coordinate system have an unknown geometric relation in that it is not known how a coordinate in the first coordinate system relates to the same coordinate in the second coordinate system, i.e., whether or not it concerns a same measured quantity, and in case of the latter, what the difference in measured quantity is.

The system 100 further comprises a processing subsystem 140. The processing subsystem 140 is shown to communicate with the input 120 via an exchange of messages 122, thereby enabling the processing subsystem 140 to access the first set of eye measurement points 050A and the first second of eye measurement points 050B. The processing subsystem 140 is configured to perform the following actions during operation of the system 100. Firstly, the processing subsystem 140 maps the first set of eye measurement points 050A and the second set of eye measurement points 050B to a common coordinate system, the mapping being based on similar coordinates being established in the common coordinate system for geometrically similar topologies of both sets of eye measurement points. The processing subsystem 140 further calculates a scene transformation for mapping the common coordinate system to a coordinate system associated with the scene, the calculating involving matching eye measurement points from the common coordinate system to interest points of the scene.

The operation of the system 100, including various optional aspects of the system 100, will be further explained with reference to FIGS. 4 to 7.

FIG. 1 shows such an optional aspect of the system 100 in that the system 100 comprises an output 160 for outputting data such as a set of gaze points 060X. The set of gaze points 060X which may be estimated by the processing subsystem 140 by mapping a set of eye measurement points, such as those of the first user or the second user, to the common coordinate system and subsequently applying the scene transformation to said set of mapped eye measurement points, thereby obtaining a set of gaze points defined in the coordinate system associated with the scene. To output such data, the processing subsystem 140 is shown to communicate with the output 160 via an exchange of messages 142. The output 160 may constitute, or be part of, e.g., a network interface, a storage interface, a display output, etc.

The output 160 may also output other data such as a difference 162 between a set of gaze points of a further user and a reference set of gaze points. This aspect of the invention will be further explained with reference to FIGS. 4 to 7.

FIG. 1 shows a further optional aspect of the system 100 in that the input 120 is shown to be arranged for obtaining an image 015 of the scene, with the processing subsystem 140 being configured for using a saliency detection technique to detect saliency points in the image so as to determine the interest points of the scene. It will be appreciated that the interest points may also be determined in various other ways as known per se in the art of eye gaze estimation. For example, instead of obtaining an image 015, the input 120 may obtain interest point data representing coordinates of the interest points in the coordinate system associated with the scene. Such coordinates may be manually determined, e.g., manually annotated, or determined automatically, e.g., using the aforementioned saliency detection.

Figure 2:
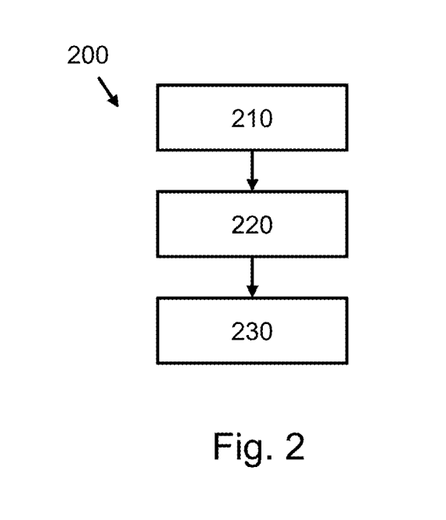
FIG. 2 shows a method in accordance with the present invention.

FIG. 2 shows a method 200 for enabling estimating gaze from a set of eye measurement points. The method 200 may correspond to an operation of the system of FIG. 1. It will be appreciated, however, that the method 200 may also be performed in separation of the system 100, e.g., using a different system or device.

The method 200 comprises, in a first step titled "OBTAINING MEASUREMENT DATA OF MULTIPLE USERS", obtaining 210 at least a first set of eye measurement points of a first user viewing the scene and a second set of eye measurement points of a second user viewing the scene. Here, the first set of eye measurement points are obtained as coordinates in a first coordinate system, the second set of eye measurement points are obtained as coordinates in a second coordinate system, and the first coordinate system and the second coordinate system have an unknown geometric relation. The method 200 further comprises, in a second step titled "MUTUALLY CALIBRATING MEASUREMENT DATA OF USERS", mapping 220 the first set of eye measurement points and the second set of eye measurement points to a common coordinate system, said mapping comprising establishing similar coordinates in the common coordinate system for geometrically similar topologies of both sets of eye measurement points. The method 200 further comprises, in a third step titled "MATCHING MUTUALLY CALIBRATED MEASUREMENT DATA TO SCENE", calculating 230 a scene transformation for mapping the common coordinate system to a coordinate system associated with the scene, said calculating comprising matching eye measurement points from the common coordinate system to interest points of the scene.

Figure 3:
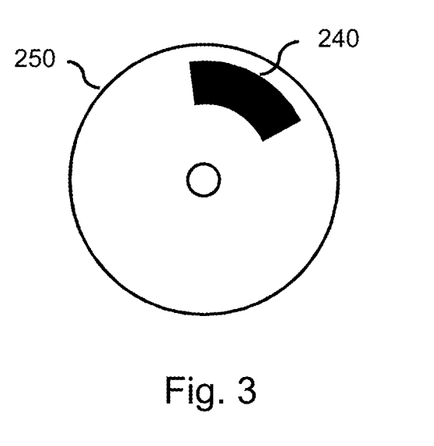
FIG. 3 shows a computer program product comprising instructions for causing a processor system to perform the method.

FIG. 3 shows a computer program product 250 comprising instructions 240 for causing a processor system to perform the method of FIG. 2. Although FIG. 3 shows the computer program product 250 in the form of an optical or magnetic disk, the computer program product 250 may also be constituted by a semiconductor memory-based device or assume any other suitable form. The instructions 240 may be comprised in a non-transitory manner on the computer program product 250, e.g., in the form of as a series of machine readable physical marks and/or as a series of elements having different electrical, e.g., magnetic, or optical properties or values.

The operation of the system of FIG. 1, the method of FIG. 2, and various optional aspects of the system and method, may be further explained as follows. It is noted that here, such operation is explained based on measurement data of three different users viewing the scene. It will be appreciated that the explanation equally holds for the use of measurement data of two different users viewing the scene.

Figure 4:
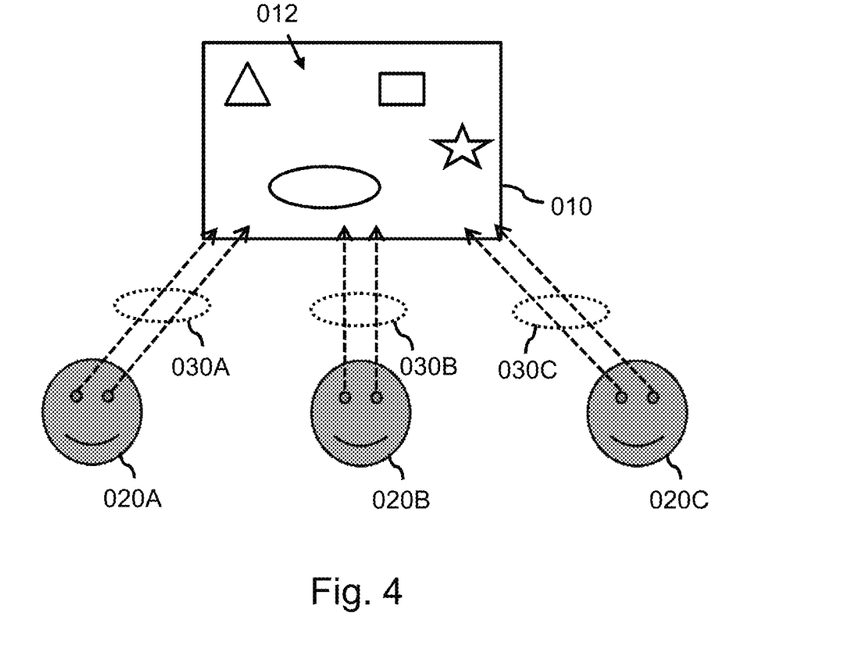
FIG. 4 illustrates different users viewing a same scene, with the scene comprising a plurality of interest points.

FIG. 4 illustrates a first user 020A, a second user 020B and a third user 020C viewing, i.e., gazing 030A-030C at, a same scene 010. The scene may be, e.g., a physical scene as presented in a shopping window, or a virtual scene as provided by content displayed on a computer screen. Although FIG. 4 shows the users 020A-020C viewing the scene 010 simultaneously, i.e., at a same time, the users 020A-020C may also view the same scene at different times, or view different instances of the same scene 010, e.g., at different locations, as displayed on different display devices, etc.

The scene is shown to comprise a plurality of interest points 012, with the interest points 012 being schematically indicated in FIG. 1 as different geometrical shapes. Such interest points constitute points in the scene which are expected to draw a user's attention. For example, in a shopping window, the user's gaze may be expected to be drawn to a product which is shown most prominently in the shopping window. The interest points 012 may be known to the system in the form of coordinates defined in a coordinate system associated with the scene.

Figure 5:
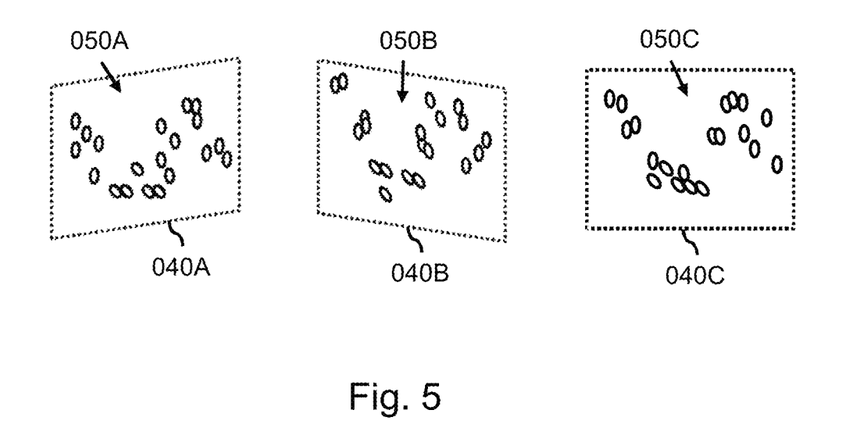
FIG. 5 shows different sets of eye measurement points as obtained from the different users, each set of eye measurement points being defined in a coordinate system, with the geometric relation between the coordinate systems being unknown.

FIG. 5 shows different sets of eye measurement points 050A-050C obtained from the different users of FIG. 4, namely a first set of eye measurement points 050A of the first user, a second set of eye measurement points 050B of the second user, and a third set of eye measurement points 050C of the third user. Each set of eye measurement points 050A-050C represents measured quantities of the respective user which are indicative of the gaze pattern of the respective user when viewing the scene. It can be seen that the three sets of eye measurement points have locally similar geometric topologies. However, there also exist individual outliers in all three sets of eye measurement points, being indicative of one or more unique gaze points of a respective user.

Each set of eye measurement points 050A-050C is defined as coordinates in a respective coordinate system 040A-040C, with the geometric relation between the coordinate systems being unknown. Typically, the coordinate systems 040A-040C differ due to the measurement data not being calibrated and thereby constituting 'raw' measurement data. FIG. 5 illustrates this difference by showing planes 040A-040C which represent the respective coordinate systems being mutually misaligned.

Figure 6:
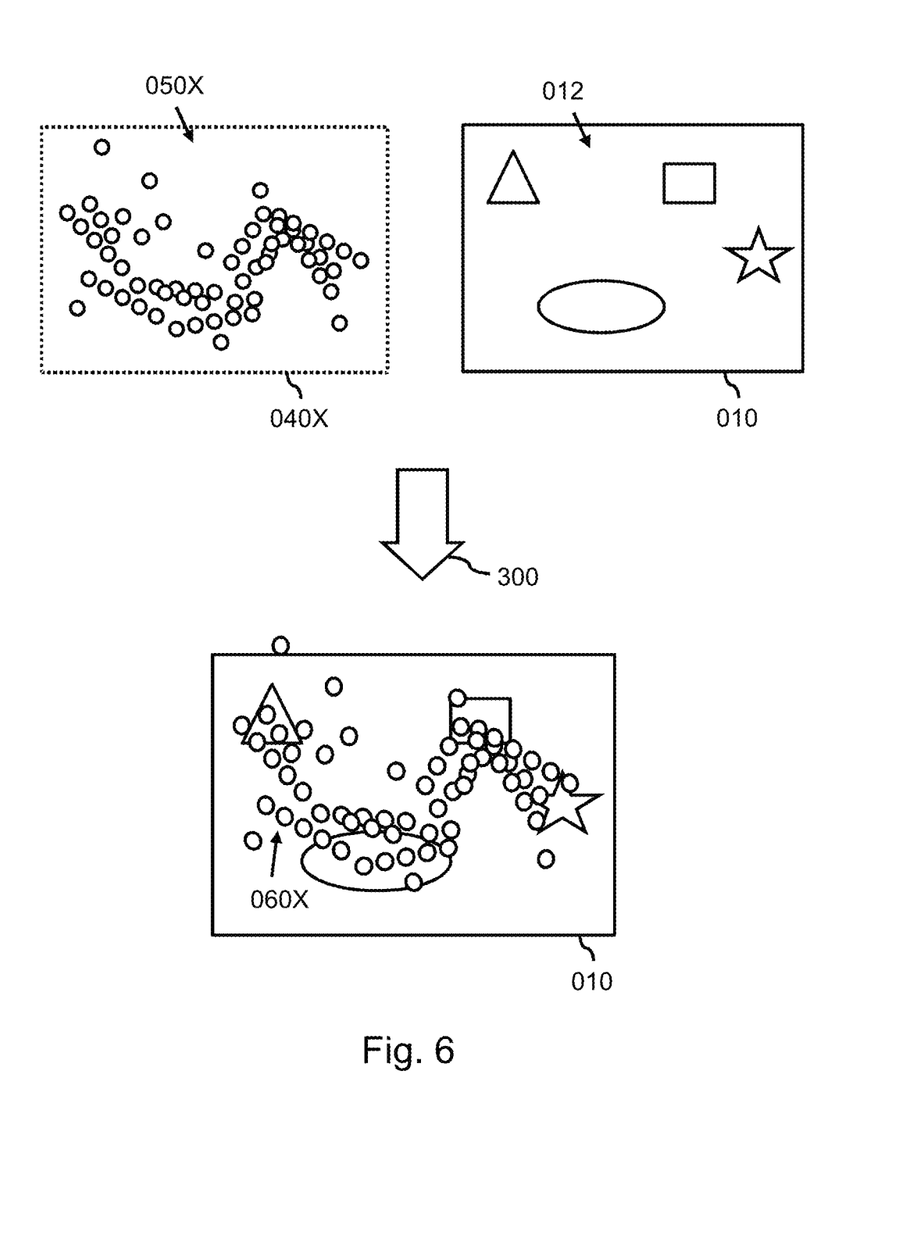
FIG. 6 illustrates a result of the different sets of eye measurement points having been mapped to a common coordinate system, and eye measurement points from the common coordinate systems having been mapped to interest points of the scene.

FIG. 6 illustrates a result of the different sets of eye measurement points having been mapped to a common coordinate system 040X, namely by showing a combined set of eye measurement points 050X in the common coordinate system 040X.

Said mapping may be performed in various ways based on the constraint that similar coordinates in the common coordinate system 040X are to be established for geometrically similar topologies of the different sets of eye measurement points. Such geometrically similar topologies may be explicitly identified. Alternatively, the mapping may involve an optimization which uses a cost function which has a relatively low cost when geometrically similar topologies of the different sets of eye measurement points are mapped to similar coordinates in the common coordinate system 040X.

For example, the mapping may be based on a so-termed K-closest point method. Here and in the following, let $\mathbb{P} = \{p^1, p^2, \ldots p^M\}$ denote the sets of eye measurement points of M different users and $p^u = \{p_1^u, p_2^u, p_3^u, \ldots, p_{un}^u,\}$ denote the set of eye measurement points of user u, with un being typically different for each user.

The K-closest point method involves finding a set of mappings $\overline{\Phi} = \{\overline{\varphi}1, \overline{\varphi}2 \ldots \overline{\varphi}M\}$ which (after applied on $\mathbb{P}$ resulting $\overline{\Phi}(\mathbb{P}) = \{\overline{\varphi}1(p^1), \overline{\varphi}2(p^2) \ldots \overline{\varphi}M(p^M)\}$) minimizes the sum of distances of each eye measurement point $\overline{\varphi}u(p_i^u)$ (where 1<i<un and 1<u<M) to its K closest neighbors of $\overline{\Phi}(\mathbb{P})$. In other words, the method solves:

$$\overline{\Phi} = \operatorname{argmin}_{\{\Phi\}}(\Gamma(\Phi(\mathbb{P}))), \qquad (1)$$

where:

$$\Gamma(\Phi(\mathbb{p})) = \sum_{u=1}^{M} \sum_{i=1}^{un} \sum_{k=1}^{K} \|\phi u(p_i^u) - N(\phi u(p_i^u), \Phi(\mathbb{p}), k)\|. \qquad (2)$$

where N(p, $\mathbb{P}$, k) is the $k^{th}$ closest point from $\mathbb{P}$ to p. Here, $\overline{\Phi}(\mathbb{P})$ represents the mutually calibrated eye measurement points of all users, i.e., the eye measurement points after being mapped to the common coordinate system, and $\overline{\Phi} = \{\overline{\varphi}1, \overline{\varphi}2 \ldots \overline{\varphi}M\}$ is the corresponding set of mappings. Note that the method tries to mutually map all sets of eye measurement points simultaneously.

The method can also be applied iteratively. In such a case, the method maps the set of eye measurement points of the first user to the common coordinate system using any mapping. From the second user on, the method finds the single mapping which maps the set of eye measurement points of a single user to the common coordinate system. An optimization method such as gradient descent may be employed to find the best set of mappings which minimizes the cost function. Note that other complex optimization methods may be applied to obtain the set of mappings.

Another example of such a mapping involves the use of a mixture model. This mixture model models the already mapped sets of eye measurement points by a Gaussian mixture and finds a single mapping which, when applied on the set of eye measurement points of a new user, maximizes the probability density function of the these mapped eye measurement points. The method works in an iterative manner.

Consider $\mathbb{P} = \{p^1, p^2 \ldots p^S\}$ are the already S mapped sets of eye measurement points of S users. The method first models $\mathbb{P}$ as a Gaussian mixture. Let $p^u = \{p_1^u, p_2^u, p_3^u, \ldots, p_{un}^u,\}$ be the set of eye measurement points of user u to be mapped to the common coordinate system. The method solves:

$$\overline{\varphi}u = \operatorname{argmax}_{\{\phi u\}}\left(\sum_{i=1}^{un} pdf(\phi u(p_i^u))\right), \qquad (3)$$

where:

$$pdf(p) = \sum_{k=1}^{K} \pi k \mathcal{N}(p \mid \mu k, \sum k). \qquad (4)$$

K is the number of model components, $\pi_k$ is the mixing coefficient of the kth Gaussian component N(p=μk,Σk) with $\mu_k$ mean and Σk covariance matrix. Here, $\overline{\varphi}u(p^u)$ represents the mutually calibrated eye measurement points of user u, i.e., the eye measurement points after being mapped to the common coordinate system.

For mapping the set of eye measurements of the first user, since there is only one set of eye measurements, any mapping may be used. The abovementioned steps can be applied for the second user on. An optimization method such as gradient descent may be employed to find the best mapping which maximizes the above optimization functions (3) and (4). Note that other complex optimization methods can be applied to obtain the mapping.

As a result, FIG. 6 shows the different sets of eye measurement points of FIG. 5 all being mapped to a common coordinate system 040X such that geometrically similar topologies of the different sets of eye measurement points have similar coordinates in the common coordinate system, i.e., their main geometric topologies overlap. In general, the mapping of the different sets of eye measurement points to the common coordinate system 040X may comprise a linear coordinate transformation.

FIG. 6 further illustrates a scene transformation 300 being calculated which maps the common coordinate system 040X to a coordinate system associated with the scene 010, namely by matching eye measurement points 050X from the common coordinate system to interest points 012 of the scene. As a result, a set of gaze points 060X is obtained which represent the eye measurement points 050X being mapped to the coordinate system of the scene 010 and thereby being calibrated with respect to the scene 010. It can be seen that the gaze points substantially follow the interest points 012 of the scene, but that also deviations from the interest points 012 exist.

Figure 7:
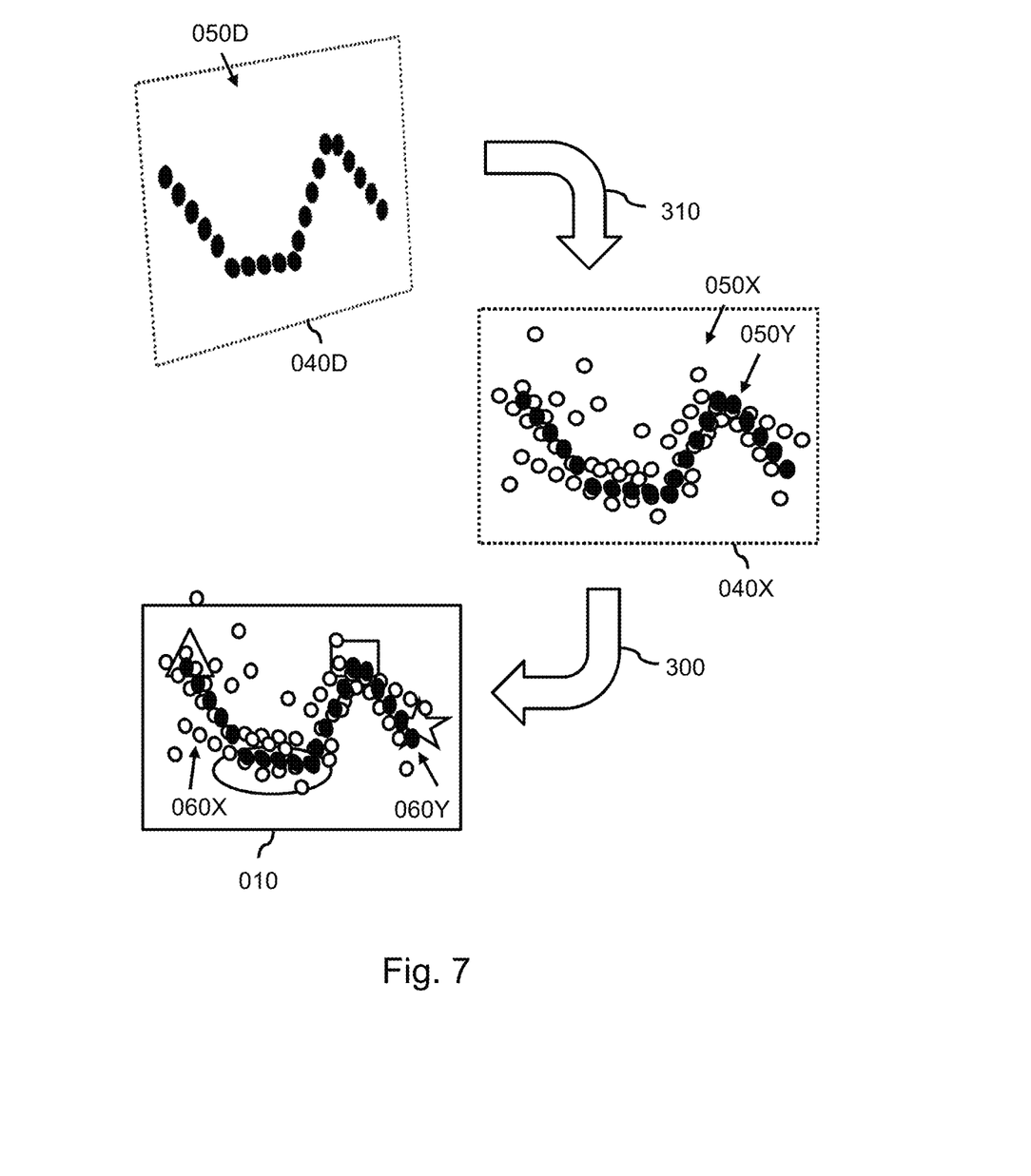
FIG. 7 illustrates a set of gaze points of a further user viewing the scene being estimated based on a further set of eye measurement points of the further user being mapped to the common coordinate system.

FIG. 7 illustrates a set of gaze points being estimated of a further user viewing the scene based on a further set of eye measurement points of the further user being mapped to the common coordinate system. This example is associated with an optional aspect of the invention, in that the input may be arranged for obtaining a further set of eye measurement points 050D of a further user viewing the scene 010. The further set of eye measurement points 050D may be defined as coordinates in a further coordinate system 040D, with the geometric relation between the further coordinate system 040D and the common coordinate system 040X not being known. The processing subsystem may be configured for mapping 310 the further set of eye measurement points 050D to the common coordinate system 040X in a similar manner as explained with reference to FIG. 6, namely based on similar coordinates being established for geometrically similar topologies. Accordingly, a further set of mapped eye measurement points 050Y may be obtained (shown in black to differentiate these from the set of mapped eye measurement points 050X), being defined by coordinates in the common coordinate system 040X. The processing subsystem may be further configured for estimating a set of gaze points 060Y of the further user by applying the scene transformation 300 to the further set of mapped eye measurement points 050Y. As a result, a set of gaze points 060Y may be obtained (shown in black to differentiate these from the set of gaze points 060X) which represent the further eye measurement points 050Y being mapped to the coordinate system of the scene 010 and thereby being calibrated with respect to the scene 010.

It will be appreciated that the different sets of mapped eye measurement points, i.e., after being mapped to the common coordinate system, may be combined to obtain a single set of reference points 050X. Such combining may involve applying a statistical filter to the different sets of eye measurement points. Having established such a set of reference points, e.g., constituted by all previously mapped eye measurement points, a further set of eye measurement points of a further user, i.e., a new user, may be mapped to the common coordinate system 040X by matching geometrically similar topologies between the further set of eye measurement points and the set of reference points. After being mapped to the common coordinate system 040X, the further set of mapped eye measurement points 050Y may be included in the set of reference points 050X so as to iteratively buildup the set of reference points. In addition, the scene transformation 300 may be re-calculated, i.e., updated, after including such a further set of mapped eye measurement points 050Y.

The processing subsystem may further be configured for identifying a difference between the set of gaze points 060Y of a further user and a reference set of gaze points 060X which is associated with the set of reference points 050X. Such a difference may involve a difference in temporal order of gazing at same or similar parts of the scene 010, or a difference in the parts of the scene at which the gazing is directed. In order to establish the former difference, the measurement data, or auxiliary data, needs to be indicative of this temporal order, e.g., by being sorted in accordance with time or by comprising a timestamp for each measurement point.

It will be appreciated that the mapping of the first set of eye measurement points and the second set of eye measurement points to a common coordinate system, i.e., the mutual calibration, may further be based on temporal information provided by each set of measurement points. A reason for this is that a gaze pattern may have a spatial topology but may also be indicative of an order or timing between the different gaze points, i.e., represent a temporal pattern. For example, a time stamp may be provided with each eye measurement point which allows such a temporal pattern to be determined. Similarities or differences between these temporal patterns may be used in the mutual calibration. For example, different users might exhibit similar temporal sub-patterns, i.e. they may view certain regions in the same order. These sub-patterns may be learnt and subsequently used to improve the mutual calibration.

It will be further appreciated that the invention may be advantageously used to auto-calibrate gaze estimators in an un-calibrated setup. Based on the observation that humans produce similar gaze patterns when looking at a stimulus, the mutually calibrated eye measurement points of several individuals and subsequent applying of the scene transformation may be used to estimate the gaze points for new viewers without active calibration.

It is noted that in general, eye measurement points represent un-calibrated measurements from which a set of gaze points may be calculated, i.e., by calibration. For example, the eye measurement points may represent changes in the user's eyes when viewing the scene. Such changes may be captured by a sensor (e.g. visual RGB camera or visual infrared camera). An eye measurement may be expressed as a scalar or a vector which may represent a state of the eye at a particular time. The measurement may contain information (features) which might be indicative of the eye gaze direction. An eye measurement point may be considered as a point representing the eye measurement in a coordinate system. Specific examples may be:

1. Relative movement of the pupil:
   a. The eye measurement may be a 3D vector representing changes of the position of the eye pupil in a 3D cartesian coordinate system. The origin (0, 0, 0) may be a fixed point. The eye pupil center may be detected using any (visual) sensor.
   b. The eye measurement may be a 3D vector representing changes of the position of the eye pupil in a 3D cylindrical coordinate system. The origin (0,0,0) may be the position of the eye pupil at time $t_0$.

2. Intensity vector of an eye image: an image showing the eye may be cropped and resized to a (L,W) crop size. The eye measurement may be a vector of the size (L*W,1) which may contain the intensity values of the cropped image. The cropped image may be divided into a A×B grid and the intensity distribution (e.g. histogram) may be computed for each grid. An eye measurement may result from combining the grid-based distributions to into a single vector. Variations may be obtained by considering color values along with/instead of intensity values.

It should be noted that the above-mentioned embodiments illustrate rather than limit the invention, and that those skilled in the art will be able to design many alternative embodiments.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for enabling estimating gaze of different users with respect to a scene from eye measurement points which represent un-calibrated eye measurements of the users viewing the scene, the system comprising:
an input for obtaining at least a first set of eye measurement points of a first user viewing the scene, and a second set of eye measurement points of a second user viewing the scene, the first set of eye measurement points being obtained as coordinates in a first coordinate system, the second set of eye measurement points being obtained as coordinates in a second coordinate system, the first coordinate system and the second coordinate system having an unknown geometric relation; and
a processing subsystem configured for:
  i) mutually calibrating the first set of eye measurement points and the second set of eye measurement points by mapping said points to a common coordinate system, thereby obtaining a set of mapped eye measurement points, said mapping includes establishing a coordinate transformation which provides similar coordinates in the common coordinate system for geometrically similar topologies of both sets of eye measurement points; and
  ii) calculating a scene transformation for mapping the common coordinate system to a coordinate system associated with the scene, said calculating includes matching eye measurement points from the set of mapped eye measurement points to interest points of the scene.

2. The system according to claim 1, wherein:
the input is arranged for obtaining a further set of eye measurement points of a further user viewing the scene, the further set of eye measurement points being obtained as coordinates in a coordinate system having an unknown geometric relation with the common coordinate system; and
the processing subsystem is configured for estimating a set of gaze points from the further set of eye measurement points by:
  i) mapping the further set of eye measurement points to the common coordinate system based on said establishing of similar coordinates for geometrically similar topologies between the further set of eye measurement points and the set of mapped eye measurement points, thereby obtaining a further set of mapped eye measurement points; and
  ii) estimating the set of gaze points of the further user by applying the scene transformation to the further set of mapped eye measurement points.

3. The system according to claim 2, wherein the processing subsystem is configured for combining the set of mapped eye measurement points and the further set of mapped eye measurement points to obtain a set of reference points, and wherein said mapping of the further set of eye measurement points to the common coordinate system is performed by the processing subsystem matching geometrically similar topologies between the further set of eye measurement points and the set of reference points.

4. The system according to claim 3, wherein the processing subsystem is configured for combining the set of mapped eye measurement points and the further set of mapped eye measurement points by applying a statistical filter to both sets of eye measurement points.

5. The system according to claim 3, wherein the processing subsystem is configured for including the further set of mapped eye measurement points in the set of reference points so as to iteratively buildup the set of reference points.

6. The system according to claim 5, wherein the processing subsystem is configured for re-calculating the scene transformation after said including of the further set of mapped eye measurement points (050Y).

7. The system according to claim 3, wherein the processing subsystem is configured for identifying a difference between the set of gaze points of the further user and a reference set of gaze points which is obtained by applying the scene transformation to the set of reference points.

8. The system according to claim 7, wherein the difference includes at least one of: a difference in temporal order of gazing at same or similar parts of the scene, and a difference in the parts of the scene at which the gazing is directed.

9. The system according to claim 1, wherein the first set of eye measurement points and the second set of eye measurement points are obtained from users viewing different instances of the scene.

10. The system according to claim 9, wherein the different instances of the scene include at least one of: the scene at different locations, a display of the scene provided by different display devices, different types of physical display of the scene.

11. The system according to claim 1, wherein the input is arranged for obtaining an image of the scene, and wherein the processing subsystem is configured for using a saliency detection technique to detect saliency points in the image so as to determine the interest points of the scene.

12. The system according to claim 1, wherein the mapping of the first set of eye measurement points and the second set of eye measurement points to the common coordinate system includes a linear coordinate transformation.

13. The system according to claim 1, wherein each set of eye measurement points is constituted by a measurement of one of the group of: a gaze direction, an iris movement, and a position of part of the eyes.

14. A method for enabling estimating gaze of different users with respect to a scene from eye measurement points which represent un-calibrated eye measurements of the users viewing the scene, the method comprising:
obtaining at least a first set of eye measurement points of a first user viewing the scene and a second set of eye measurement points of a second user viewing the scene, the first set of eye measurement points being obtained as coordinates in a first coordinate system, the second set of eye measurement points being obtained as coordinates in a second coordinate system, the first coordinate system and the second coordinate system having an unknown geometric relation;
mutually calibrating the first set of eye measurement points and the second set of eye measurement points by mapping said points to a common coordinate system, thereby obtaining a set of mapped eye measurement points, said mapping include establishing a coordinate transformation which provides similar coordinates in the common coordinate system for geometrically similar topologies of both sets of eye measurement points; and
calculating a scene transformation for mapping the common coordinate system to a coordinate system associated with the scene, said calculating includes matching eye measurement points from the set of mapped eye measurement points to interest points of the scene.

15. A non-transitory computer readable medium comprising a computer program product, the computer program product comprising instructions for causing a processor system to perform the method according to claim 14.

\* \* \* \* \*